(12) United States Patent
Larson et al.

(10) Patent No.: US 10,245,212 B2
(45) Date of Patent: Apr. 2, 2019

(54) VIAL HOLDER DEVICES, METHODS AND SYSTEMS

(71) Applicant: Orbit Biomedical Limited, London (GB)

(72) Inventors: Chaley Larson, Horsham, PA (US); Kostadinka Lilova, Spring House, PA (US); Mike Cannamela, New York, NY (US); William Cagney, Horsham, PA (US); Gordon Kosovan, Raritan, NJ (US); Elaine Hughes, Horsham, PA (US); Maria Ficchi, Malvern, PA (US)

(73) Assignee: Orbit Biomedical Limited, London (GB)

( * ) Notice: Subject to any disclaimer, the term of this patent is extended or adjusted under 35 U.S.C. 154(b) by 378 days.

(21) Appl. No.: 14/975,161

(22) Filed: Dec. 18, 2015

(65) Prior Publication Data

US 2016/0175197 A1 Jun. 23, 2016

Related U.S. Application Data

(60) Provisional application No. 62/093,887, filed on Dec. 18, 2014.

(51) Int. Cl.
*A61B 17/06* (2006.01)
*A61J 1/16* (2006.01)
(Continued)

(52) U.S. Cl.
CPC .............. *A61J 1/16* (2013.01); *A61B 50/20* (2016.02); *A61B 50/30* (2016.02); *A61B 90/90* (2016.02);
(Continued)

(58) Field of Classification Search
CPC .............. B65D 23/0885; B65D 25/205; B65D 77/0446; A61J 1/16; A61J 2205/30;
(Continued)

(56) References Cited

U.S. PATENT DOCUMENTS 4,840,618 A * 6/1989 Marvel ............... A61M 5/3213
604/187
5,330,439 A * 7/1994 Jackson .................... B01L 9/06
211/74

(Continued)

FOREIGN PATENT DOCUMENTS

CN 101934878 A 1/2011
CN 102575214 A 7/2012
(Continued)

OTHER PUBLICATIONS

Chinese Office Action dated Aug. 27, 2018 for Application No. 201580069171.2, 5 pages.
(Continued)

*Primary Examiner* — Luan K Bui
(74) *Attorney, Agent, or Firm* — Frost Brown Todd LLC

(57) ABSTRACT

A packaging apparatus is provided for holding a sterile product. In one aspect, a secondary packaging holder is configured with a base and a receiving portion to receive and irreversibly hold a primary packaging holder. The secondary packaging holder can have a substantially planar wall configured to affix an identifying label thereto. The secondary packaging holder can be configured to snap fit to a neck of the primary packaging holder to hold the primary packaging holder such that a portion of the primary packaging holder is exposed outside of the secondary packaging holder based on a height relationship between the secondary packaging holder and the primary packaging holder.

29 Claims, 6 Drawing Sheets

(51) Int. Cl.
*B65B 3/00* (2006.01)
*B65D 23/08* (2006.01)
*B65D 25/20* (2006.01)
*B65D 77/04* (2006.01)
*A61B 50/20* (2016.01)
*A61B 50/30* (2016.01)
*A61B 90/90* (2016.01)
*A61B 90/96* (2016.01)

(52) U.S. Cl.
CPC .............. *B65B 3/003* (2013.01); *B65B 3/006* (2013.01); *B65D 23/0885* (2013.01); *B65D 25/205* (2013.01); *B65D 77/0446* (2013.01); *A61B 90/96* (2016.02); *A61J 2205/30* (2013.01); *B65B 2220/16* (2013.01)

(58) Field of Classification Search
CPC ......... A61B 50/20; A61B 50/30; A61B 90/90; A61B 90/96
USPC ............... 206/438, 446, 459.5; 604/192, 263
See application file for complete search history.

(56) References Cited

U.S. PATENT DOCUMENTS

| | | | |
|---|---|---|---|
| 5,934,099 A | 8/1999 | Cook et al. | |
| 6,662,941 B2 | 12/2003 | Lowry et al. | |
| 7,175,055 B2* | 2/2007 | Hansen | A61M 5/14546 222/325 |
| 8,230,997 B1 | 7/2012 | McWilliams et al. | |
| 8,292,075 B2* | 10/2012 | Liao | A61C 8/0087 206/438 |
| 8,479,919 B2* | 7/2013 | Kaplan | B65D 51/002 206/438 |
| 2003/0024895 A1 | 2/2003 | Meyers et al. | |
| 2004/0112781 A1* | 6/2004 | Hofverberg | A61C 8/0087 206/438 |
| 2007/0181446 A1 | 8/2007 | Donahoe et al. | |
| 2008/0164273 A1* | 7/2008 | Dallman | A61J 7/0069 221/2 |
| 2010/0038273 A1 | 2/2010 | Johnson | |
| 2012/0053528 A1* | 3/2012 | Bollenbach | A61M 5/24 604/192 |
| 2012/0065611 A1 | 3/2012 | Musani | |
| 2014/0246349 A1 | 9/2014 | Adler et al. | |
| 2014/0263319 A1 | 9/2014 | Fazi et al. | |
| 2015/0083626 A1* | 3/2015 | Dallman | B65D 51/002 206/438 |
| 2015/0084252 A1* | 3/2015 | Dallman | A61J 1/16 269/5 |
| 2017/0095403 A1 | 4/2017 | Larson et al. | |

FOREIGN PATENT DOCUMENTS

| | | |
|---|---|---|
| WO | WO-96-036437 A1 | 11/1996 |
| WO | WO-2016-100808 A1 | 6/2016 |
| WO | WO-2016-100808 R | 6/2016 |

OTHER PUBLICATIONS

European Search Report and Written Opinion dated Oct. 23, 2018 for Application No. 15871161.4, 7 pages.
International Search Report and Written Opinion dated Mar. 20, 2018 for International Application No. PCT/US2017/064807, 8 pages.

* cited by examiner

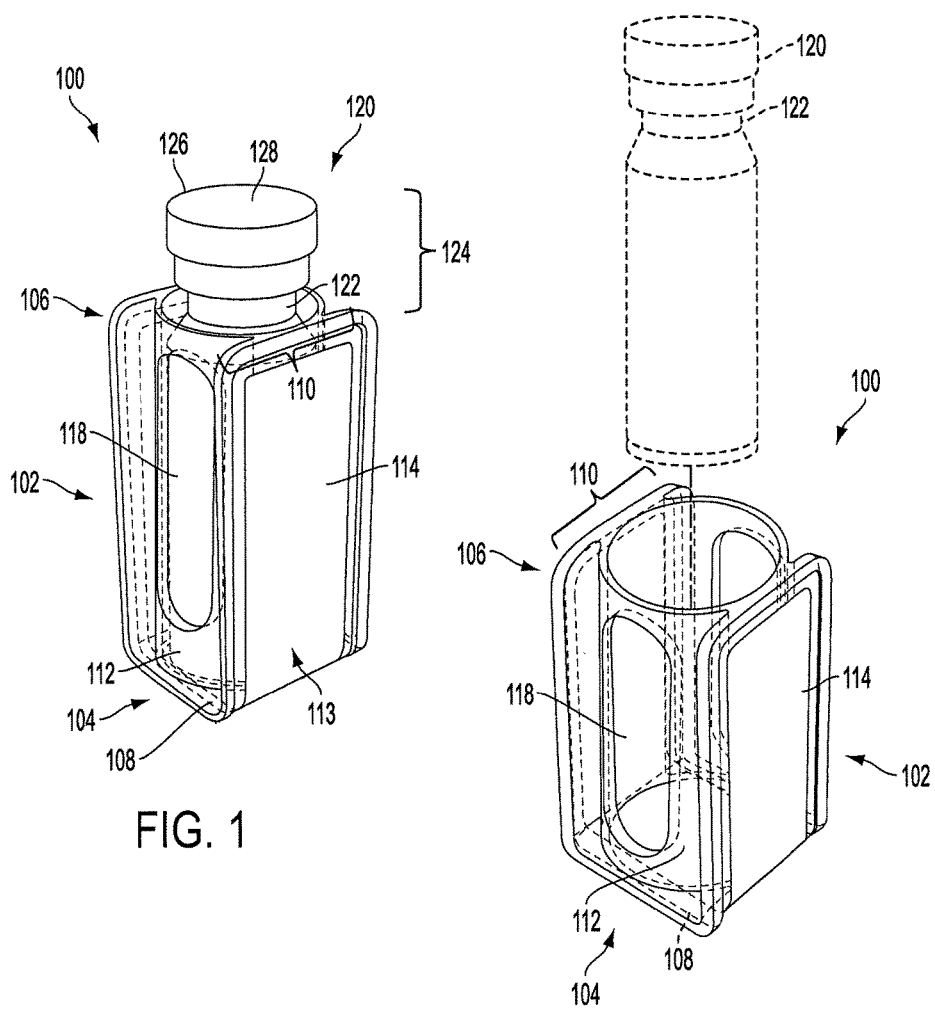

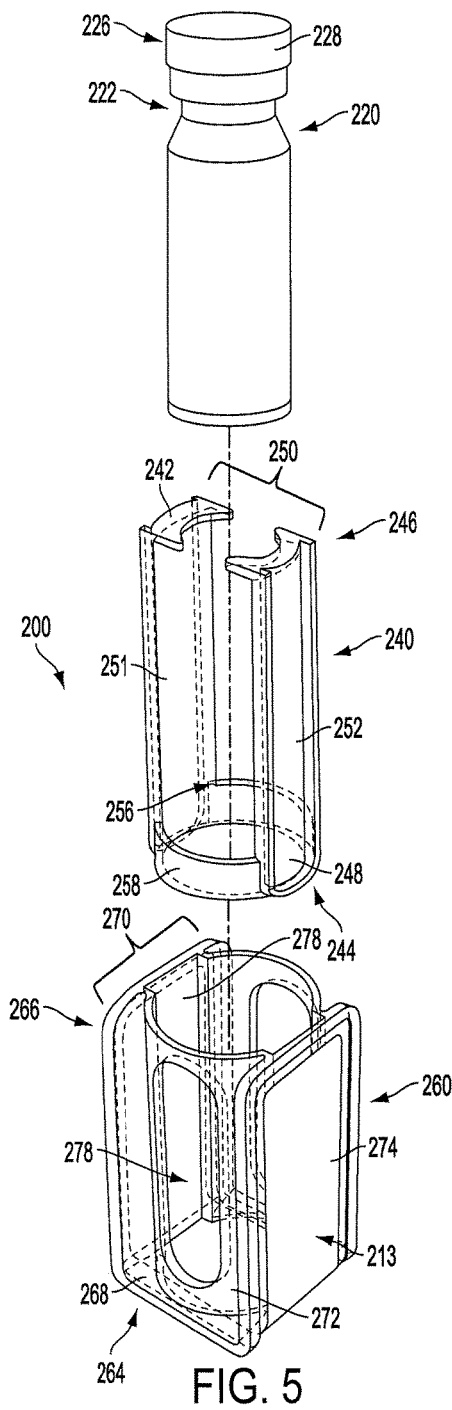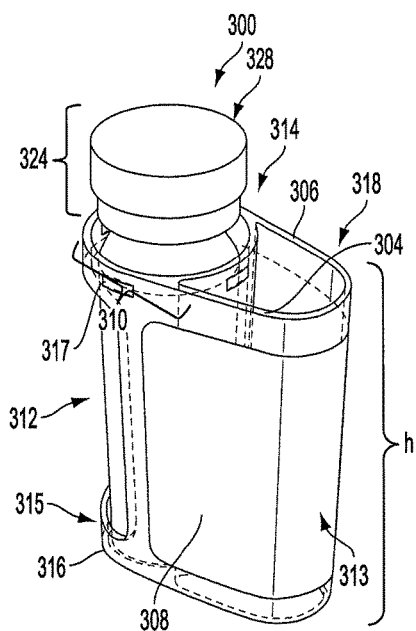
FIG. 5
FIG. 6

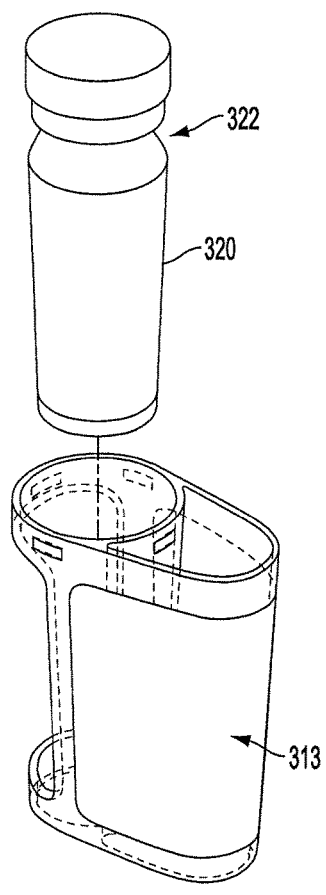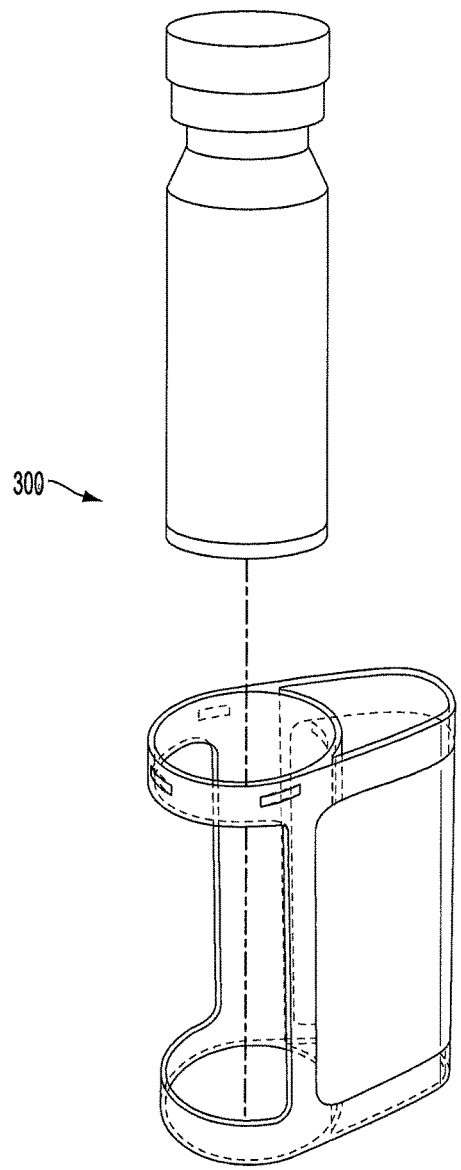
FIG. 7
FIG. 8

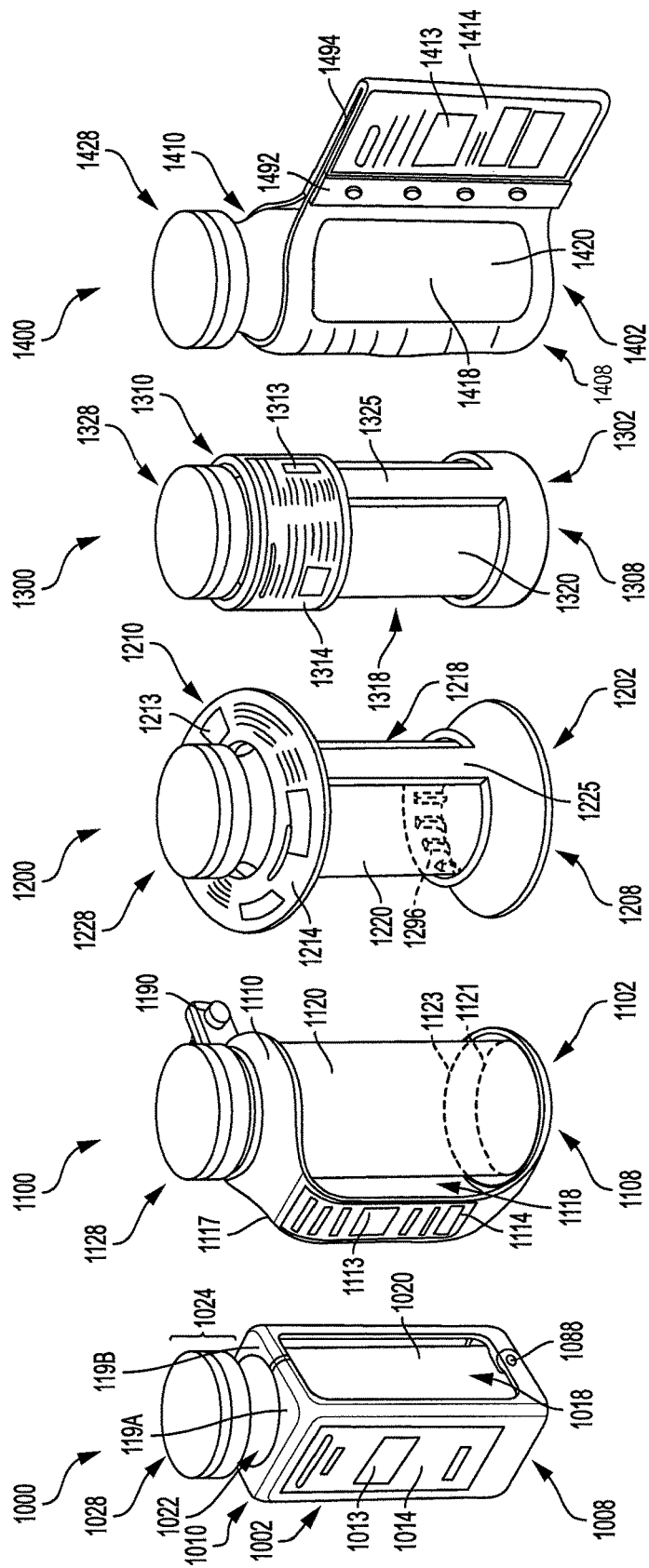

VIAL HOLDER DEVICES, METHODS AND SYSTEMS

CROSS-REFERENCE TO RELATED APPLICATIONS

This application claims benefit of U.S. Provisional Application Ser. No. 62/093,887, filed on Dec. 18, 2014, the entire content of which is incorporated by reference herein in its entirety.

TECHNICAL FIELD

The present invention relates to devices, methods and systems for use with vials and storage of a sterile product.

BACKGROUND

Vials containing agents, medicine, products or biological and/or chemical agents are fragile and require careful handling. Further, because common shapes of vials are cylindrical, it can be difficult to label the vials, for example, when vials are labeled in bulk. Specialized equipment or manual labor has been employed to label vials. However, current labelling of vials remains cumbersome and expensive. Further, the storage of bulk vials can require bulky equipment to make sure that the vials do not tip over and spill.

What is needed are devices, methods and systems for efficient packaging and labelling of a vial and/or a sterile product.

SUMMARY

In one aspect of the present invention, a packaging apparatus for holding a sterile product includes a secondary packaging holder having a base at a first end and a receiving portion at an opposing second end. The secondary packaging holder can be configured to receive and securely and irreversibly hold a primary packaging holder. The packaging apparatus can include at least one substantially planar wall that extends from the first end to the second end. The at least one substantially planar wall can be configured to affix an identifying label thereto. An interior of the secondary packaging holder can be configured to securely and irreversibly hold the primary packaging holder. When the primary packaging holder is securely and irreversibly held, the primary packaging holder can have a portion exposed outside of the secondary packaging holder based on a height relationship between the secondary packaging holder and the primary packaging holder.

The secondary packaging holder can be configured to snap fit to a neck of the primary packaging holder to securely and irreversibly hold the primary packaging holder.

At least one non-planar wall can extend from a side of the base different from the at least one substantially planar wall. The at least one non-planar wall can extend from the first end to the second end.

Each of the non-planar walls can outline an aperture along a substantial portion of a longitudinal axis of the non-planar wall.

In another aspect of the present invention, a packaging system for housing a sterile product can include a secondary packaging holder having a primary packaging holder receiving portion at a first end. The secondary packaging holder can be configured to securely and irreversibly hold a portion of a primary packaging holder that is configured to hold a sterile product. The packaging system can include a tertiary packaging holder having a base and having a secondary packaging holder receiving portion at an opposing end. The tertiary packaging holder can be configured to receive and securely and irreversibly hold the secondary packaging holder. The tertiary packaging holder can include at least one substantially planar wall extending from the first end to the second end of the tertiary packaging holder. The substantially planar wall can have an exterior surface configured to affix an identifying label thereto.

The primary packaging holder receiving portion can have a region with at least a portion of an interior surface having an arc-shape that is configured to receive and hold a primary packaging holder having a substantially cylindrical shape.

The secondary packaging holder can have a base at a second end opposite to the first end, and can have at least one substantially planar wall that extends from the first end to the second end of the secondary packaging holder.

The base of the tertiary packaging holder can be rectangular and the at least one substantially planar wall can extend from at least one side of the base.

The at least one substantially planar wall can extend from the first end to the second end of the tertiary packaging holder. An interior surface of the at least one planar wall of the tertiary packaging can contact an exterior surface of the at least one surface of the secondary packaging holder.

Two substantially planar walls of the tertiary packaging holder can extend from respective sides of the base to the secondary packaging holder receiving portion. Further, two substantially planar walls of the secondary packaging holder can extend from the respective sides such that interior surfaces of the two substantially planar walls of the tertiary packaging holder contact exterior surfaces of the two substantially planar walls of the secondary packaging holder.

Two non-planar walls of the tertiary packaging holder can extend from other respective sides of the base to the secondary packaging holder receiving portion.

Each of the non-planar walls of the tertiary packaging holder can outline an aperture in a middle section of the non-planar wall. Further, spacings in between the two planar walls of the secondary packaging holder can overlap with the apertures when the secondary packaging holder is securely and irreversible held. The overlapped apertures and spacings can allow for direct access through the walls on the side.

The apertures can allow for direct access to at least a portion of a side of the primary packaging holder when the primary packaging holder is securely and irreversibly held in the secondary packaging holder and tertiary packaging holder.

The spacings of the secondary packaging holder can extend from the primary packaging holder receiving portion to a lip on the base.

The base of the secondary packaging holder along each spacing can include a lip that borders the base in between the substantially planar walls and that extends towards the first end.

The lips of the secondary packaging holder can be configured to contact an interior surface of substantially arc-shaped walls of the tertiary packaging holder.

The primary packaging holder can be a necked cylinder, and the secondary packaging holder can have shoulders configured to irreversibly snap fit at the neck of the primary packaging holder.

The primary packaging holder can include a sealable port configured to enclose an interior space of the primary packaging holder when sealed. The secondary and tertiary packaging holders can permit direct access to the interior space via the port.

The tertiary packaging holder can have an external profile configured to permit close packing of a plurality of tertiary packaging holders in at least two dimensions.

The primary packaging holder can be a vial.

In another aspect of the present invention, a packaging apparatus for housing a sterile product can include a substantially cylindrical vial holder having a receiving portion at a first end and a base at a second opposing end. The packaging apparatus can include a stand that is adjacent to the substantially cylindrical vial holder. The stand can have a cross-section that is different than a cross-section of the cylindrical vial holder. The packaging apparatus can include lock-in units that are disposed on an interior surface of the receiving portion. The lock-in units can be configured to lock in a vial once the vial has been inserted into the cylindrical vial holder a predetermined amount. The substantially cylindrical vial holder can have a height that allows for a user to remove a vial holder lid after the vial has been locked-in.

The stand can be formed by a first wall that is integral with the cylindrical vial holder and that extends in a tangential plane from a longitudinal line at a first point along the cylindrical vial holder and a second wall that is integral with the cylindrical vial holder and that extends in a tangential plane from a longitudinal line at a substantially opposing point than the first point along the cylindrical vial holder. Exterior surfaces of the first and second walls include at least one substantially planar labelling surface configured to affix an adhesive label thereto.

The first and second walls can join in a substantially rounded manner forming an arc-shaped curve. The arc-shaped curve can have a circular portion that has a smaller arc-length than an arc-length of the cylindrical vial holder.

In another aspect of the present invention, a method of packaging a sterile product can include providing a primary packaging holder having a sterile interior space and a sealable port. The method can include depositing a sterile product in the interior space via the port. The method can include receiving the primary packaging holder through a receiving portion of a secondary packaging holder such that the secondary packaging holder securely and irreversibly holds the primary packaging holder. The method can include receiving the secondary packaging holder through a receiving portion of a tertiary packaging holder such that the tertiary unit (packaging holder) securely and irreversibly holds the secondary unit (packaging holder). The method can be such that the tertiary packaging holder includes a substantially planar exterior surface that is configured to affix an identifying label thereto.

The depositing of a sterile product in the interior space can occur after securing the primary packaging holder to the secondary packaging holder. The depositing a sterile product in the interior space can occur after securing the secondary packaging holder to the tertiary packaging holder.

The method can further include affixing an identifying label to the substantially planar exterior surface of the tertiary packaging holder.

The secondary packaging holder can be configured to snap fit to a neck of the primary packaging holder to securely and irreversibly hold the primary packaging holder.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

FIG. 1 shows a secondary packaging holder holding a primary packaging holder, according to an embodiment of the invention.

FIG. 2 shows a perspective view of a secondary packaging holder with the primary packaging holder outside the secondary packaging holder, according to an embodiment of the invention.

FIG. 5 shows an exploded view of a tertiary packaging holder, a secondary packaging holder and a primary packaging holder, according to an embodiment of the invention.

FIG. 6 shows a secondary packaging holder holding a primary packaging holder, in accordance with an embodiment of the invention.

FIG. 7 shows an exploded view of the secondary packaging holder and the primary packaging holder of FIG. 6.

FIG. 8 shows an alternative perspective of FIG. 7.

FIG. 10 shows a secondary packaging holder and a primary packaging holder, according to an embodiment of the invention.

FIG. 11 shows a secondary packaging holder and a primary packaging holder, according to an embodiment of the invention.

FIG. 12 shows a secondary packaging holder and a primary packaging holder, according to an embodiment of the invention.

FIG. 13 shows a secondary packaging holder and a primary packaging holder, according to an embodiment of the invention.

FIG. 14 shows a secondary packaging holder and a primary packaging holder, according to an embodiment of the invention.

Figure 3:
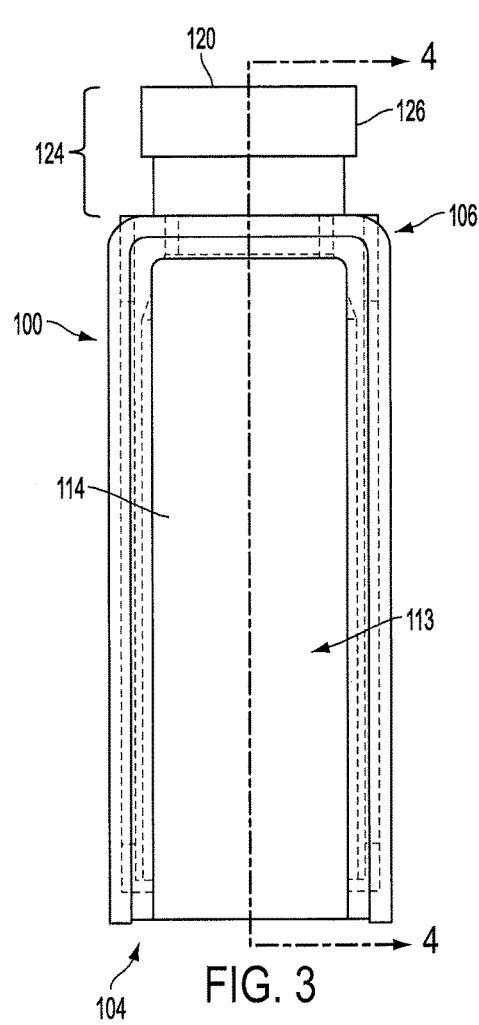
FIG. 3 shows a side view of FIG. 1, according to an embodiment of the invention.

These and other features and advantages will be apparent from a reading of the following detailed description and a review of the associated drawings. It is to be understood that both the foregoing general description and the following detailed description are explanatory only and are not restrictive of aspects as claimed.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention.

The term "securely" is intended to have a broad meaning that may be used in holding packaging units. A primary packaging holder can be "securely" held by a secondary packaging holder when the secondary packaging holder is sized to hold the primary packaging holder without allowing movement of the primary unit relative to the secondary packaging holder. Similarly, a secondary packaging holder can be "securely" held by a tertiary packaging holder when the tertiary packaging holder is sized to hold the secondary packaging holder without allowing movement of the secondary packaging holder relative to the tertiary packaging holder.

The term "irreversibly" is intended to have a broad meaning as, for example, configured to remain as assembled during normal use; tamper evident.

The term "primary packaging holder" is intended to have a broad meaning as, for example, a packaging unit or device configured to hold a sterile product and maintain sterility of the sterile product during handling, storage, and transportation.

The term "secondary packaging holder" is intended to have a broad meaning as, for example, a packaging unit or device configured to hold a primary packaging holder, in particular to securely and irreversibly hold the primary packaging holder.

The term "tertiary packaging holder" is intended to have a broad meaning as, for example, a packaging unit or device configured to hold a secondary packaging holder, in particular to securely and irreversibly hold the secondary packaging holder.

The term "non-enclosing" is intended to have a broad meaning as, for example, a secondary and/or tertiary packaging holder is non-enclosing if at least a portion of the exterior of the primary packaging holder is accessible without disrupting the secondary and/or tertiary packaging holder.

The term "direct access" is intended to have a broad meaning as, for example, access to an interior space of a primary packaging holder without the need to open, disrupt or tamper with a secondary or tertiary packaging holder.

FIG. 1 shows an embodiment of the present invention. FIG. 1 shows a perspective view of a packaging apparatus 100 for holding a sterile product. The packaging apparatus 100 can include a secondary packaging holder 102 having a base 108 at a first end 104 and a receiving portion 110 at an opposing second end 106. The secondary packaging holder 102 can be configured to receive and securely and irreversibly hold a primary packaging holder 120. The packaging apparatus 100 can be configured to provide an area adapted for labeling and/or providing identification information, preferably, directed to primary packaging holder 120. As shown, packaging apparatus 100 can include at least one substantially planar wall 114 that can extend from the first end 104 to the second end 106. The at least one substantially planar wall 114 can be configured to affix an identifying label thereto.

An interior of the secondary packaging holder 102 can be configured to receive the primary packaging holder 120 and to snap fit to a neck 122 of the primary packaging holder 120 to securely and irreversibly hold the primary packaging holder 120. The primary packaging holder 120 can be permanently secured in the secondary packaging holder 102. When the primary packaging holder 120 is securely and irreversibly held, the primary packaging holder 120 can have a portion 124 exposed outside of the secondary packaging holder 102. As shown, the exposed portion 124 can be based on a height relationship between the secondary packaging holder 102 and the primary packaging holder 120. This can allow for the secondary packaging holder 102 not to interfere with the integrity of a cap 128 of the primary packaging holder 120. The height relationship between the secondary packaging holder 102 and the primary packaging holder 120 can also allow for the secondary packaging holder 102 not to interfere with removal of the cap 128. For example, when the primary packaging holder 120 is being securely and irreversibly held, an entirety of the cap 128 can be exposed outside the secondary packaging holder 102 allowing for removal of the cap 128. Further, product from the primary packaging holder 120 can also be removed without regard to interference from the secondary packaging holder 102.

The secondary packaging holder 102 can be made of plastic or other sturdy and resilient materials. The secondary packaging holder 102 can be transparent or opaque. In an embodiment, at least one non-planar wall 112 can extend from a side of the base 108 different from the at least one substantially planar wall 114 of the secondary packaging holder 102. The at least one non-planar wall 112 can extend from the first end 104 to the second end 106. The secondary packaging holder 102 can allow for the primary packaging holder 120 to be thawed within the secondary packaging holder 102 in a variety of thaw mechanisms. For example, thawing can take place in a customized dry heater block to fit to the shape of the secondary packaging holder 102. Further, for example, thawing can take place in a saline bath or at room temperature.

Each of the non-planar walls 112 can outline an aperture 118 along a substantial portion of a longitudinal axis of the non-planar wall 112. The aperture 118 can provide for direct access to the primary packaging holder 120. The primary packaging holder 120 can include a sealable port 126 configured to enclose an interior space of the primary packaging holder 120 when sealed. In one embodiment, the sealable port can be sealed by the cap 128. The secondary and tertiary packaging holders (see FIG. 5) permit direct access to the interior space via the sealable port 126.

FIG. 1 shows an identifying label 113 affixed to the secondary packaging holder for illustration purposes. In some embodiments, however, the identifying label 113 is not part of the secondary packaging holder 102. The identifying label 113 can be a primary label that can be used to identify the product of the primary packaging holder 120. The identifying label can be permanently affixed to the secondary packaging holder 102. As shown, the secondary packaging holder 102 can be a vial holder. The secondary packaging holder 102 and the identifying label can be designed with tamper evident features. Once the primary packaging holder 120 has been inserted into the secure and irreversible position, the primary packaging holder 120 in one embodiment cannot be removed without noticeably destroying or damaging the secondary packaging holder 102. The secondary packaging holder 102 can accept the primary packaging holder 120. The primary packaging holder 120 can be a vial. For example, the vial can be a frozen, un-labeled product vial. The vial can be without a label and the vial identification unique to that vial can be included on the label 113. Various information about the vial and/or the vial contents can be included on the label, such as, lot number, serial number, etc.

Assembly of the primary packaging holder 120 into the secondary packaging holder 102 can be rapid and can be performed with gloved hands and/or tools. Based on the ability for the primary packaging holder 120 and the secondary packaging holder 102 to be assembled, the packaging apparatus 100 can allow for the allowable temperature exposure time for a drug product contained in the primary packaging holder 120 to not be exceeded. The plurality of vials can be at a site of secondary packaging and distribution. The assembly process can allow for advantages. With regard to supply chain, first, the packaging apparatus can move labelling operations outside a predetermined manufacturing time window. For example, a predetermined manufacturing time window can be three hours. Next, labeling can be co-located with the secondary packaging holder 102 and can be applied at the same time as the secondary packaging holder 102 receives the primary packaging holder 120. Through the inventive principles described herein, investment of specialized labeler/robotics and serialization equipment and/or other machinery can be avoided or mitigated. Additionally, segregation of country-specific labeled product during long-term storage can be avoided or mitigated.

The packaging apparatus has additional commercial and regulatory advantages as well. For example, labeling for specific markets can occur closer to a customer. The labeling can be better aligned with forecast/orders and can allow for more flexibility for demand changes. Further, a label can be designed to meet country-specific regulatory and language requirements. Thus, the packaging apparatus can be multifunctional, can be user-friendly, and can include distinguished branding.

The packaging apparatus 100 allows for increased surface area for labeling. Further, the packaging apparatus 100 by having a substantially planar surface for which to affix the identifying label can provide for an improved label adhesion at room temperature. The identifying label that the packaging apparatus is configured to affix can meet country-specific regulatory and language requirements for all markets. Information on the label can take on various forms including, for example, text and/or machine readable code, sensors, etc. The identifying label can be adhesive. In another embodiment, the identifying label can be printed directly onto the substantially planar surface. In one embodiment, labeling of the secondary packaging holder can be performed either manually or in an automated way.

The packaging apparatus 100 allows for a customizable, injection mold design where many sizes and style options are possible. The shape of the packaging apparatus can leverage cryo-cart or similar environment through an assembly operation for the handling of frozen drug product. Rapid, manual operation can be utilized to limit product exposure to ambient temperatures. Small, customized "batch operations" can be utilized using the packaging apparatus to fulfill regional orders as needed. The vial can be permanently secured in the secondary packaging holder by means of a quick, "snap-fit" assembly. In some embodiments, the snap-fit assembly consists of the secondary packaging holder having shoulders that irreversibly snap fit at a neck 122 of a primary packaging holder 120. Other portions of the secondary packaging holder 102 and primary packaging holder 120 interacting are possible as well, including, for example, the base of the secondary packaging holder snapping into the bottom portion of the primary packaging holder 120. The base of the secondary packaging holder 102 can provide for a stable presentation of the packaging apparatus 100. The stable presentation can result from a lower center of gravity, for example, caused by a weight of the base. FIG. 2 shows an exploded representation of a primary packaging holder 120 outside of a secondary packaging holder 102.

FIG. 3 shows a side view of the packaging apparatus 100. FIG. 3 shows that the primary packaging holder 120 is in a received position of the secondary packaging holder 102. As can be seen, the at least one substantially planar walls 114 can be in a rectangular shape that extends from a side of the base of the first end 104 to the second end 106.

Figure 4:
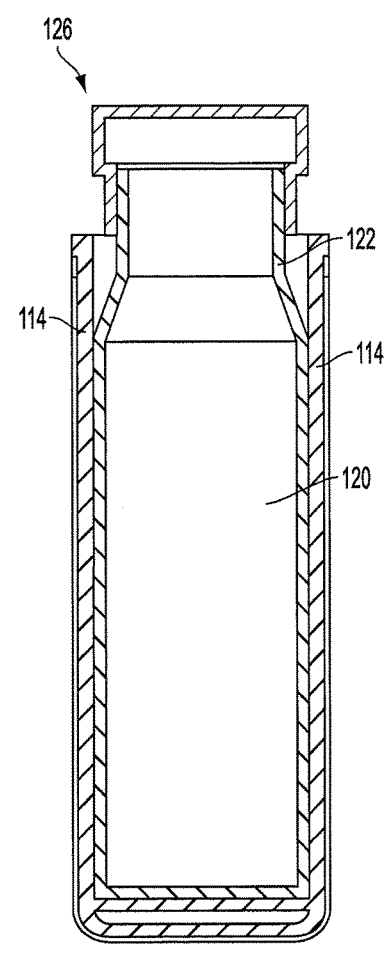
FIG. 4 shows a cross section along line 4-4 of FIG. 3, according to an embodiment of the invention.

FIG. 4 shows a cross section of FIG. 3. As can be seen from FIG. 4, primary packaging holder 120 can make contact with a substantial portion of its exterior surface with an interior surface of the secondary packaging holder 102. The secondary packaging holder 102 can include two substantially planar walls 114.

FIG. 5 shows another embodiment of the invention. FIG. 5 shows a packaging system 200 for housing a sterile product that can include a secondary packaging holder 240 having a primary packaging holder-receiving portion 250 at a first end 246. The secondary packaging holder 240 can be configured to securely and irreversibly hold a portion of a primary packaging holder 220 that is configured to hold a sterile product. The packaging system 200 can also include a tertiary packaging holder 260 having a base 268 and having a secondary packaging holder receiving portion 270 at an opposing end 266 to the base 268. The tertiary packaging holder can be configured to receive and securely and irreversibly hold the secondary packaging holder.

The tertiary packaging holder 260 can include substantially planar wall 274 extending from the base 268 to the opposing end 266 of the tertiary packaging holder 260. The substantially planar wall 274 can have an exterior surface configured to affix an identifying label 213 thereto. In one embodiment, the tertiary packaging holder 260 can have two substantially planar walls 274.

The height relationship between the secondary packaging holder 240 and the primary packaging holder 220 can allow for the secondary packaging holder 240 to not interfere with removal of the cap 228 of the primary packaging holder 220. For instance, when the primary packaging holder 220 is securely and irreversibly held, the primary packaging holder 220 can have a portion exposed outside of the secondary packaging holder 240 to allow the secondary packaging holder 240 to not interfere with the integrity of the cap 228 of the primary packaging holder 220. Cap 228 attaches to the top end 226 of primary packaging holder 220. In another embodiment, the height relationship between the secondary packaging holder 240 and the primary packaging holder 220 can allow for the secondary packaging holder 240 to interfere with removal of the cap 228. In yet another embodiment, the height of the secondary packaging holder 240 can be approximately the same as the height of the tertiary packaging holder 260.

The primary packaging holder receiving portion 250 can have a region 242 with at least a portion of an interior surface having an arc-shape. The region 242 can be configured to receive and hold a primary packaging holder having a cylindrical shape. In one embodiment, the primary packaging holder can be a vial that houses a sterile product.

The secondary packaging holder 240 can be made of plastic or other sturdy and resilient materials. The secondary packaging holder 240 can be transparent or opaque. The secondary packaging holder 240 can have a base 248 at a second end 244 opposite to the first end 246, and at least one substantially planar wall 252 that extends from the first end 246 to the second end 244 of the secondary packaging holder 240.

The tertiary packaging holder 260 can be made of plastic or other sturdy and resilient materials. The tertiary packaging holder 260 can be transparent or opaque. The base 268 of the tertiary packaging holder 260 can be rectangular and the at least one substantially planar wall 274 of the tertiary packaging holder 260 can extend from at least one side of the base 268.

The at least one substantially planar wall of the tertiary packaging holder 260 can extend from the base 268 to the opposing end 266 of the tertiary packaging holder 260. An interior surface of the at least one planar wall 274 of the tertiary packaging holder 260 can contact an exterior surface of the at least one surface of the secondary packaging holder 240.

In one embodiment, two substantially planar walls 274 of the tertiary packaging holder 260 can extend from respective sides of the rectangular base 268 to the secondary packaging holder receiving portion 270. Further, two substantially planar walls 252 of the secondary packaging holder 240 can extend from the respective sides such that interior surfaces of the two substantially planar walls 274 of the tertiary packaging holder 260 can contact exterior surfaces of the two substantially planar walls 252 of the secondary packaging holder 240 in a received position.

In one embodiment, two non-planar walls 272 of the tertiary packaging holder 260 can extend from other respective sides of the rectangular base 268 to the secondary packaging holder receiving portion 270. Each of the non-planar walls 272 of the tertiary packaging holder 260 can outline an aperture 278 located in a middle section of each of the non-planar walls 272. Spacings 256 in between the two planar walls 252 of the secondary packaging holder 240 can overlap with the apertures 278 of the tertiary packaging holder 260 when the secondary packaging holder 240 is securely and irreversibly held. The overlapped apertures and spacings allowing for direct access through the walls on the side to the primary packaging holder when the primary packaging holder 220 is securely and irreversibly held in the secondary packaging holder 240 and the tertiary packaging holder 260. Thus, the apertures can allow for direct access to at least a portion of a side of the primary packaging holder 220 when the primary packaging holder 220 is securely and irreversibly held in the secondary packaging holder 240 and tertiary packaging holder 260.

The spacings 256 of the secondary packaging holder 240 can extend from the primary packaging holder receiving portion 250 to a lip 258 on the base. The base 248 of the secondary packaging holder 240 along each of the spacings 256 can include a lip 258 that borders the base 248 and that extends along the longitudinal axis in between the planar surfaces. The lip 258 of the secondary packaging holder 240 can be configured to contact an interior surface 251 of substantially arc-shaped walls of the tertiary packaging holder 260. In some embodiments, the secondary packaging holder 240 can be configured to snap fit into the tertiary packaging holder 260.

The primary packaging holder can be a necked cylinder, and the secondary packaging holder can have shoulders configured to irreversibly snap fit at a neck 222 of the primary packaging holder 220. Other portions of the secondary packaging holder 240 and primary packaging holder 220 interacting are possible as well, including, for example, the base of the secondary packaging holder 240 snapping into the bottom portion of the primary packaging holder 220.

The packaging unit can include a sealable port 126 configured to enclose an interior space of the primary packaging holder when sealed. The secondary and tertiary packaging holders permit direct access to the interior space via the sealable port 126.

The tertiary packaging holder can have an external profile configured to permit close packing of a plurality of tertiary packaging holders in at least two dimensions.

FIG. 6 shows that in another embodiment, a packaging apparatus 300 for housing a sterile product can include a secondary packaging holder comprises a substantially cylindrical vial holder 312 having a receiving portion 310 at a first end 314 and a base 316 at a second opposing end. The packaging apparatus 300 can include a label stand 318 that is adjacent to the substantially cylindrical vial holder 312. The label stand 318 can have a cross-section shape that is different than a cross-section shape of the substantially cylindrical vial holder. For example, rather than having a circular cross-section, the label stand 318 can be a substantially non-uniform cross-section shape. As can be seen from FIG. 6, a portion of the label stand 318 cross-section shape can share an edge with the substantially cylindrical vial holder portion. Thus, the label stand 318 cross section can be concave.

The height relationship between the secondary packaging holder 312 and the primary packaging holder 320 can allow for the secondary packaging holder 312 to not interfere with removal of the cap 328 of the primary packaging holder 320. For instance, when the primary packaging holder 320 (see FIG. 7) is securely and irreversibly held, the primary packaging holder 320 can have a portion 324 exposed outside of the secondary packaging holder 312 to allow the secondary packaging holder 312 not to interfere with the integrity of cap 328 of the primary packaging holder 320. In another embodiment, the height relationship between the secondary packaging holder 312 and the primary packaging holder 320 can allow for the secondary packaging holder 312 to interfere with removal of the cap 328.

The packaging apparatus 300 can include lock-in units 317 that are disposed on an interior surface of the receiving portion 310. The lock-in units 317 can be configured to lock in a vial 320 (see FIG. 7) once the vial 320 has been inserted into the cylindrical vial holder 312 a predetermined amount. For example, a predetermined amount can be until the vial has been inserted up until a neck 322 of the vial. Through the lock-in units 317, the vial 320 can be snap fit into the substantially cylindrical vial holder 312.

The substantially cylindrical vial holder 312 can have a height h that allows for a user to remove a vial holder lid after the vial has been locked-in. The secondary packaging holder/vial holder 312 can include at least one region 315 of the base 316 that is configured to encircle a bottom portion of the primary packaging holder 320. For example, as shown in FIG. 6, this region 315 of the base 316 borders an aperture of the secondary packaging holder 312.

The label stand 318 can be formed by a first wall 304 that is integral with the cylindrical vial holder 312 and that extends in a tangential plane from a longitudinal line at a first point along the cylindrical vial holder and a second wall 306 that is integral with the cylindrical vial holder and that extends in a tangential plane from a longitudinal line at a substantially opposing point than the first point along the cylindrical vial holder 312. In one embodiment, exterior surfaces of the first and second walls 304, 306 can include at least one substantially planar labelling surface 308 configured to affix an identifying label 313 thereto. The first and second walls 304, 306 can join in a substantially rounded manner forming an arc-shaped curve. The arc-shaped curve can have a circular portion that has a smaller arc-length than an arc-length of the cylindrical vial holder.

FIG. 7 shows an exploded view of the secondary packaging holder, and FIG. 8 shows an alternative perspective of the exploded view of FIG. 7. While FIGS. 6-8 show label 313, it is to be understood that this is for illustrative purposes only and that label 313 is not part of the secondary packaging holder.

Figure 9:
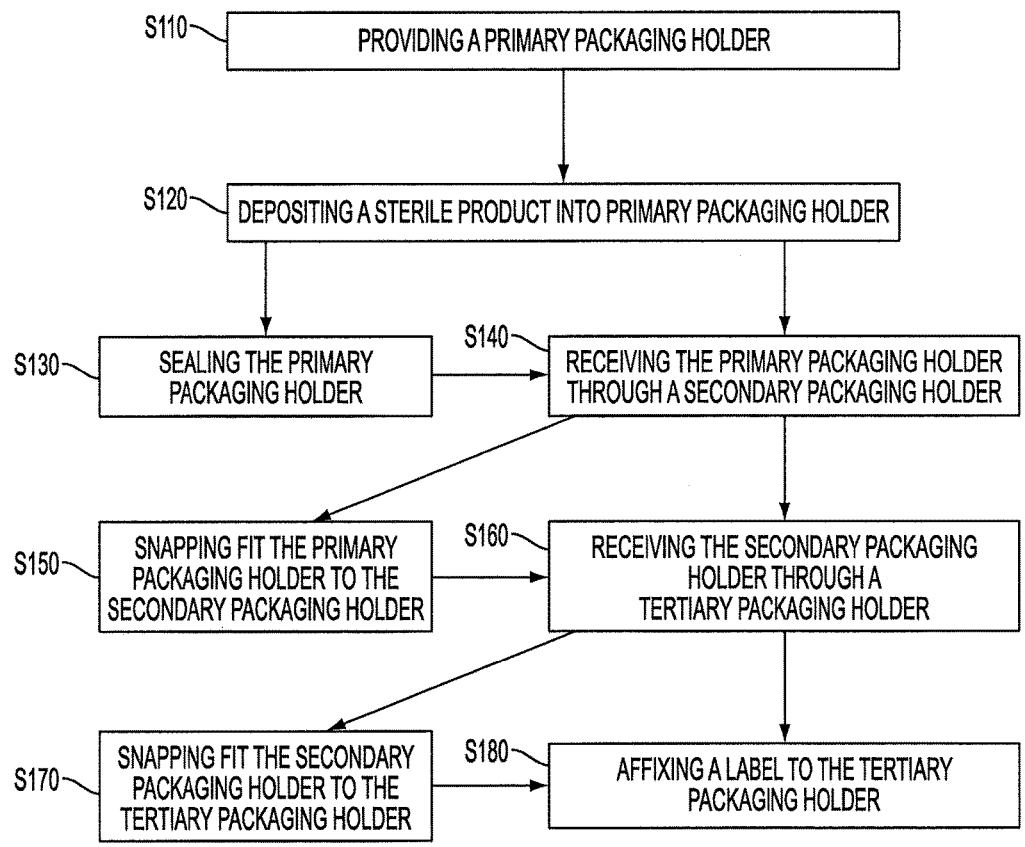
FIG. 9 shows a method of packaging a sterile product in accordance with an embodiment of the invention.

In another embodiment, FIG. 9 shows a method of packaging a sterile product. The method can include in step S110 providing a primary packaging holder. The primary packaging holder can have a sterile interior space and a sealable port. The method can include step S120 depositing a sterile product. The step S120 can include depositing into the interior space through the port. The method can include S130 sealing the port. The port can be sealed by securing a cap on the primary packaging holder. The method can further include S140 receiving the primary packaging holder through a receiving portion of a secondary packaging holder. The method can further include S150 snapping fit the primary packaging holder to the secondary packaging holder. The steps S140 and S150 can be such that the secondary packaging holder securely and irreversibly holds the primary packaging holder. The method can further include S160 receiving the secondary packaging holder through a receiving portion of a tertiary packaging holder. The step S160 can be such that the tertiary unit securely and irreversibly holds the secondary unit. The tertiary packaging holder can include a substantially planar exterior surface that is configured to affix an identifying label thereto. The method can include S170 snapping fit the secondary packaging holder to the tertiary packaging holder.

The method can further include step S180 affixing a label to the tertiary packaging holder. The method can further include affixing an identifying label to the substantially planar exterior surface of the tertiary packaging holder. The exterior surface can be substantially planar. The identifying label can be an adhesive label.

The depositing a sterile product in the interior space can take place after securing the primary packaging holder to the secondary packaging holder. The depositing a sterile product in the interior space can also occur after securing the secondary packaging holder to the tertiary packaging holder.

FIGS. 10-14 show alternative embodiments of packaging apparatuses. In an embodiment as shown in FIG. 10, the packaging apparatus 1000 can include a secondary packaging holder 1002 that is configured to hold a primary packaging holder 1020. In this embodiment, similar to embodiments described heretofore, the secondary packaging holder 1002 can have a substantially cuboid exterior shape. The secondary packaging holder 1002 can be made of two halves 119A and 119B that can connect by means of a hinge pin 1088 near a base 1008 of the secondary packaging holder 1002. As seen from FIG. 10, the base 1008 can be square-shaped. The hinge pin 1088 can be used to lock the two halves together. Embodiments of the invention contemplate various configurations for locking the two halves together using the hinge pin such as, for example, pressing the two halves together or by pressing the hinge pin, for example, by a user. The secondary packaging holder 1002 can have a circularly-shaped opening near a top portion to snap fit to a neck 1022 of the body and cap 1028 of the primary packaging holder 1020.

The secondary packaging holder 1002 can include one surface 1014 that may be substantially planar. The surface 1014 can be configured such that a label 1013 can adhere thereto. The secondary packaging holder 1002 can outline an aperture 1018 on one or more sides from the base 1008 to the receiving portion 1010.

In an embodiment as shown in FIG. 11, the packaging apparatus 1100 can include a secondary packaging holder 1102 that has a circular base 1108 and a circular receiving portion 1110. The base 1108 can have an outer diameter that substantially conforms to the outer diameter of a primary packaging holder 1120. Similarly, the receiving portion 1110 can have an inner diameter that substantially conforms to the outer diameter of the primary packing holder 1120. The circular base 1108 can have a lower rim 1121 and an upper rim 1123. The secondary packaging holder 1102 can connect the base 1108 to a receiving portion 1110 by means of a connecting portion 1117. In an embodiment, the connecting portion 1117 can extend outwardly from the base and have a generally planar portion or surface 1114 configured to receive a label 1113 thereto. Thus, when inserted, a gap 1118 between the primary packaging holder 1120 and the connecting portion 1117 of the secondary packaging holder 1102 can be more pronounced than the distance between the regions near the receiving portion 1110 and the base 1108. The primary packaging holder 1120 has a cap 1128.

The secondary packaging holder 1102 can outline an aperture 1118 around a majority of the secondary packaging holder 1102 from the base 1108 to the receiving portion 1110. After receiving the primary packaging holder 1120, the secondary packaging holder 1102 can secure the primary packaging holder 1120 by means of a ratchet pin 1190. Embodiments of the invention contemplate various configurations for locking the secondary packaging holder 1102 using the ratchet pin. The ratchet pin 1190 can work by snapping the pin to lock, for example, by a user. For example, the ratchet pin 1190 can be located at the receiving portion 1110.

In an embodiment as shown in FIG. 12, the packaging apparatus 1200 can include a secondary packaging holder 1202 that has a circular base 1208 and a circular receiving portion 1210. In an embodiment, the circular base 1208 has a diameter that is substantially larger than a diameter of a primary packaging holder 1220 that is configured to be received therein. Similarly, the receiving portion 1210 can have a diameter that is substantially larger than the outer diameter of the primary packaging holder 1220. The secondary packaging holder 1202 can connect the base 1208 to the receiving portion 1210 by means of at least one side panel 1225. The secondary packaging holder 1220 can be configured such that at least one aperture 1218 is formed between the base 1208 and the receiving portion 1210. The primary packaging holder 1220 has a cap 1228.

In an embodiment, the receiving portion can include a substantially planar region 1214 that is configured to receive at least one label 1213. The base 1208 can include crush ribs 1296 that can allow for the secondary packaging holder 1202 to securely and tightly fit the primary packaging holder 1220. Embodiments of the invention contemplate various configurations for locking the secondary packaging holder 1202. For example, the primary packaging holder 1220 can be pushed to interact with the crush ribs and thus lock the primary packaging holder 1220 inside the secondary packaging holder 1202.

In an embodiment as shown in FIG. 13, the packaging apparatus 1300 can include a secondary packaging holder 1302 that has a circular base 1308 and a circular receiving portion 1310. The base 1308 can have an inner diameter that substantially conforms to the outer diameter of a primary packaging holder 1320. Similarly, the receiving portion 1310 can have an inner diameter that substantially conforms to the outer diameter of the primary packing holder 1320. The secondary packaging holder 1302 can connect the base 1308 to the receiving portion 1310 by means of at least one side panel 1325. The secondary packaging holder 1320 can be configured such that at least one aperture 1318 is formed between the base 1308 and the receiving portion 1310. The primary packaging holder 1320 has a cap 1328.

Towards the receiving portion 1310, as seen from FIG. 13, a region 1314 that spans at least a portion of a surface of the secondary packaging holder 1302 can be configured to adhere at least one label 1313 thereto. The secondary packaging holder 1302 can have flex arms that slide and snap to lock the secondary packaging holder 1302. Embodiments of the invention contemplates various configurations of using the flex arms to slide and snap to lock, thus securely and tightly fitting the primary packaging holder 1320 inside the secondary packaging holder 1302.

In an embodiment as shown in FIG. 14, the packaging apparatus 1400 can include a secondary packaging holder 1402 that has at least a partially circular base 1408 and at least a partially circular receiving portion 1410. In an embodiment, the secondary packaging holder 1402 includes a stand 1494 that projects outwardly from a side of the secondary packaging holder 1402. The stand 1494 can include at least one buttons or locking mechanisms 1492 that are configured to be snapped to lock the primary packaging holder 1420 inside the secondary packaging holder 1402. The stand 1494 can include at least one substantially planar surface 1414 that is configured to receive at least one label 1413. The primary packaging holder 1420 has a cap 1428.

The secondary packaging holder 1402 can outline at least one aperture 1418 from the base 1408 to the receiving portion 1410. The secondary packaging holder 1402 can include a flexible mesh. While FIGS. 10-14 show labels 1013, 1113, 1213, 1313, 1413, respectively, the identifying labels are for illustrative purposes only and are not part of the secondary packaging holders 1002, 1102, 1202, 1302, 1402.

In describing embodiments, specific terminology is employed for the sake of clarity. However, the invention is not intended to be limited to the specific terminology and examples selected. A person skilled in the relevant art will recognize that other equivalent components can be employed and other methods developed without departing from the broad concepts of the current invention.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

We claim:

1. A packaging apparatus for holding a sterile product comprising:
   (a) a primary packaging holder configured to hold a sterile product therein,
   wherein the primary packaging holder includes:
      (i) a body including a bottom surface,
      (ii) a neck having a smaller cross-sectional area than the body, and
      (iii) a top end having a larger cross-sectional area than the neck;
   (b) a secondary packaging holder having configured to hold the primary packaging holder, wherein the secondary packaging holder includes:
      (i) a base at a first end disposed adjacent the bottom surface of the primary packaging holder, and
      (ii) a receiving portion at an opposing second end, wherein the receiving portion includes first and second arc-shaped regions configured to securely retain the neck of the primary packaging holder therebetween, wherein the first and second arc shaped regions are configured to move relative to each other; wherein the top end of the primary packaging holder is exposed outside of the secondary packaging holder based on a height relationship between the secondary packaging holder and the primary packaging holder;
   (c) a tertiary packaging holder configured to hold the secondary packaging holder, wherein the tertiary packaging holder includes:
      (i) a base at a first end,
      (ii) first and second substantially planar opposing walls extending from the base of the tertiary packaging holder, wherein the first and second substantially planar opposing walls have an exterior surface; and
   (d) an identifying label attached to the exterior surface of the first and second substantially planar opposing walls.

2. The packaging apparatus of claim 1, wherein the first and second arc-shaped regions of the secondary packaging holder are configured to snap fit together to securely and irreversibly hold the primary packaging holder.

3. The packaging apparatus of claim 1, further comprising:
   first and second opposing walls that extend between the base and the receiving portion, and
   first and second opposing lips that each extend from sides of the base different from the first and second substantially planar opposing walls.

4. The packaging apparatus of claim 3, wherein each of the first and second opposing lips outline an aperture along a longitudinal axis of the lip.

5. A packaging system for housing a sterile product comprising:
   (a) a primary packaging holder configured to hold a sterile product therein, wherein the primary packaging holder includes:
      (i) a body including a bottom surface,
      (ii) a neck having a smaller cross-sectional area than the body, and
      (iii) a top end having a larger cross-sectional area than the neck;
   (b) a secondary packaging holder configured to hold the primary packaging holder, wherein the secondary packaging holder includes:
      (i) a primary packaging holder receiving portion at a first end, wherein the primary packaging holder receiving portion is configured to securely hold the neck of the primary packaging holder,
      (ii) a base at a second end configured to receive the bottom surface of the primary packaging holder, and
      (iii) first and second opposing walls extending between the base and the primary packaging holder receiving portion; and
   (c) a tertiary packaging holder configured to hold the secondary packaging holder, wherein the tertiary packaging holder includes:
      (i) a base at a first end configured to receive the base of the secondary packaging holder,
      (ii) a secondary packaging holder receiving portion at an opposing end, wherein the secondary packaging holder receiving portion is configured to receive and securely and irreversibly hold the secondary packaging holder,
      (iii) first and second substantially planar opposing walls extending from the first end of the tertiary packaging holder to a second end of the tertiary packaging holder, wherein the first and second substantially planar opposing walls have an exterior surface configured to affix an identifying label thereto, and
      (iv) first and second opposing walls extending between the first and second substantially planar opposing walls, wherein the first opposing wall of the tertiary packaging holder outlines a first aperture in a middle section of the first opposing wall of the tertiary packaging holder, and wherein spacings in between the first and second opposing walls of the secondary packaging holder are configured to overlap with the first aperture.

6. The packaging system of claim 5, wherein the primary packaging holder receiving portion has a region with at least a portion of an interior surface having an arc-shape that is configured to receive and hold the neck of the primary packaging holder having a substantially cylindrical shape.

7. The packaging system of claim 5, wherein the first and second opposing walls of the secondary packaging holder include first and second substantially planar opposing walls that extend from the first end to the second end of the secondary packaging holder.

8. The packaging system of claim 7, wherein the base of the tertiary packaging holder is rectangular and wherein the first and second substantially planar opposing walls extend from the base.

9. The packaging system of claim 8, wherein:
an interior surface of the first and second substantially planar walls of the tertiary packaging holder contact an exterior surface of the secondary packaging holder.

10. The packaging system of claim 9, wherein:
the first and second substantially planar opposing walls of the tertiary packaging holder extend from respective sides of the base of the tertiary packaging holder to the secondary packaging holder receiving portion, and
the first and second substantially planar opposing walls of the secondary packaging holder extend from the respective sides such that interior surfaces of the first and second substantially planar walls of the tertiary packaging holder contact exterior surfaces of the first and second substantially planar walls of the secondary packaging holder.

11. The packaging system of claim 10, wherein the first and second opposing walls of the tertiary packaging holder include first and second non-planar walls of the tertiary packaging holder extend from other respective sides of the base to the secondary packaging holder receiving portion.

12. The packaging system of claim 11, wherein:
each of the non-planar walls of the tertiary packaging holder outlines an aperture in a middle section of the non-planar wall, and
spacings in between the first and second planar opposing walls of the secondary packaging holder overlap with the apertures when the secondary packaging holder is securely and irreversible held.

13. The packaging system of claim 12, wherein the apertures allow for direct access to at least a portion of a side of the primary packaging holder when the primary packaging holder is securely and irreversibly held in the secondary packaging holder and tertiary packaging holder.

14. The packaging system of claim 12, wherein the spacings of the secondary packaging holder extend from the primary packaging holder receiving portion to a lip on the base of the secondary packaging holder.

15. The packaging system of claim 12, wherein the base of the secondary packaging holder along each spacing includes a lip that borders the base of the secondary packaging holder in between the substantially planar walls and that extends towards the first end.

16. The packaging system of claim 15, wherein the lips of the secondary packaging holder are configured to contact an interior surface of substantially arc-shaped walls of the tertiary packaging holder.

17. The packaging system of claim 5, wherein the primary packaging holder is a necked cylinder, and wherein the secondary packaging holder has shoulders configured to irreversibly snap fit at the neck of the primary packaging holder.

18. The packaging system of claim 5, wherein:
the primary packaging holder includes a sealable port configured to enclose an interior space of the primary packaging holder when sealed; and
the secondary and tertiary packaging holders permit direct access to the interior space via the port.

19. The packaging system of claim 5, wherein the tertiary packaging holder has an external profile configured to permit close packing of a plurality of tertiary packaging holders in at least two dimensions.

20. The packaging system of claim 5, wherein the primary packaging holder is a vial.

21. The packaging system of claim 5, wherein the second opposing wall of the tertiary packaging holder outlines a second aperture in a middle section of the second opposing wall of the tertiary packaging holder, and wherein spacings in between the first and second opposing walls of the secondary packaging holder are configured to overlap with the second aperture.

22. The packaging system of claim 5, wherein the primary packaging holder receiving portion includes at least first and second arc-shaped regions configured to securely retain the neck of the primary packaging holder therebetween, wherein the first and second arc shaped regions are configured to move relative to each other.

23. A packaging system configured to house a primary packaging holder containing a sterile product, the packaging system comprising:
(a) a secondary packaging holder configured to hold the primary packaging holder, wherein the secondary packaging holder includes:
(i) a primary packaging holder receiving portion at a first end, wherein the primary packaging holder receiving portion is configured to securely hold the primary packaging holder,
(ii) a base at a second end, and
(iii) first and second opposing walls extending between the base and the primary packaging holder receiving portion; and
(b) a tertiary packaging holder configured to hold the secondary packaging holder, wherein the tertiary packaging holder includes:
(i) a base at a first end configured to receive the base of the secondary packaging holder,
(ii) a secondary packaging holder receiving portion at an opposing end, wherein the secondary packaging holder receiving portion is configured to receive and securely hold the secondary packaging holder,
(iii) first and second substantially planar opposing walls extending from the first end of the tertiary packaging holder to the second end of the tertiary packaging holder, wherein the first and second substantially planar opposing walls have an exterior surface configured to affix an identifying label thereto, and
(iv) first and second opposing walls extending between the first and second substantially planar opposing walls, wherein the first opposing wall of the tertiary packaging holder outlines a first aperture in a middle section of the first opposing wall of the tertiary packaging holder, and wherein spacings in between the first and second opposing walls of the secondary packaging holder are configured to overlap with the first aperture.

24. The packaging system of claim 23, wherein the second opposing wall of the tertiary packaging holder outlines a second aperture in a middle section of the second opposing wall of the tertiary packaging holder, and wherein spacings in between the first and second opposing walls of the secondary packaging holder are configured to overlap with the second aperture.

25. The packaging system of claim 23, wherein the primary packaging holder receiving portion includes at least first and second arc-shaped regions configured to securely retain the neck of the primary packaging holder therebetween, wherein the first and second arc shaped regions are configured to move relative to each other.

26. The packaging system of claim 23, wherein the base of the tertiary packaging holder is rectangular and wherein the substantially planar wall extends from at least one side of the base.

27. The packaging system of claim 23, wherein the apertures allow for direct access to at least a portion of a side of the primary packaging holder when the primary packaging holder is securely and irreversibly held in the secondary packaging holder and tertiary packaging holder.

28. The packaging system of claim 23, wherein the spacings of the secondary packaging holder extend from the primary packaging holder receiving portion to a lip on the base.

29. The packaging system of claim 23, wherein the base of the secondary packaging holder includes an aperture extending completely therethrough.

\* \* \* \* \*